United States Patent [19]

Kaali et al.

[11] Patent Number: 5,188,738

[45] Date of Patent: * Feb. 23, 1993

[54] ALTERNATING CURRENT SUPPLIED ELECTRICALLY CONDUCTIVE METHOD AND SYSTEM FOR TREATMENT OF BLOOD AND/OR OTHER BODY FLUIDS AND/OR SYNTHETIC FLUIDS WITH ELECTRIC FORCES

[76] Inventors: Steven Kaali, 88 Ashford Ave., Dobbs Ferry, N.Y. 10522; Peter M. Schwolsky, 4101 Cathedral Ave., NW., Washington, D.C. 20016

[*] Notice: The portion of the term of this patent subsequent to Aug. 18, 2009 has been disclaimed.

[21] Appl. No.: 615,437

[22] Filed: Nov. 16, 1990

Related U.S. Application Data

[63] Continuation-in-part of Ser. No. 562,721, Aug. 6, 1990, abandoned.

[51] Int. Cl.⁵ .................. B01D 35/06; A61K 41/00
[52] U.S. Cl. ..................... 210/748; 128/419 R; 128/421; 128/783; 128/784; 204/131; 204/164; 204/186; 204/302; 210/243; 422/22; 422/44; 604/4
[58] Field of Search .......... 210/243, 748, 764; 128/419 R, 421, 783, 784; 604/4; 422/22, 44; 204/131, 164, 186, 242, 275, 302, 305

[56] References Cited

U.S. PATENT DOCUMENTS

| | | | |
|---|---|---|---|
| 592,735 | 10/1897 | Jones | 204/242 |
| 672,231 | 4/1901 | Lacomme | 204/275 |
| 2,490,730 | 12/1949 | Dubilier | 204/305 |
| 3,692,648 | 9/1972 | Matloff et al. | 204/129 |
| 3,753,886 | 8/1973 | Myers | 204/186 |
| 3,878,564 | 4/1975 | Yao et al. | 210/648 |
| 3,965,008 | 6/1976 | Dawson | 422/22 |
| 3,994,799 | 11/1976 | Yao et al. | 210/321.64 |
| 4,473,449 | 9/1984 | Michaels et al. | 204/101 |
| 4,616,640 | 10/1986 | Kaali et al. | 128/130 |
| 4,770,167 | 9/1988 | Kaali et al. | 128/788 |
| 4,932,421 | 6/1990 | Kaali et al. | 128/831 |
| 5,049,252 | 9/1991 | Murrell | 210/243 |
| 5,058,065 | 10/1991 | Slovak | 128/783 |
| 5,133,932 | 7/1992 | Gunn et al. | 210/748 |

FOREIGN PATENT DOCUMENTS

995848 7/1983 U.S.S.R. .................. 210/243

OTHER PUBLICATIONS

Proceedings of the Society for Experimental Biology & Medicine, vol. 1, (1979), pp. 204–209, "Inactivation of Herpes Simples Virus with Methylene Blue, Light and Electricity"—Mitchell R. Swartz et al.

Journal of the Clinical Investigation published by the American Society for Clinical Investigations, Inc., vol. 65, Feb. 1980, pp. 432–438—"Mechanisms of Photodynamic Inactivation of Herpes Simplex Viruses"—Lowell E. Schnipper et al.

Journal of Clinical Microbiology, vol. 17, No. 2, Feb. 1983, pp. 374–376, "Photodynamic Inactivation of Pseudorabier Virus with Methylene Blue Dye, Light and Electricity"—Janine A. Badyisk et al.

Primary Examiner—Robert A. Dawson
Assistant Examiner—Sun Uk Kim
Attorney, Agent, or Firm—Charles W. Helzer

[57] ABSTRACT

A new alternating current process and system for treatment of blood and/or other body fluids and/or synthetic fluids from a donor to a recipient or storage receptacle or in a recycling system using novel electrically conductive treatment vessels for treating blood and/or other body fluids and/or synthetic fluids with electric field forces of appropriate electric field strength to provide electric current flow through the blood or other body fluids at a magnitude that is biologically compatible but is sufficient to render the bacteria, virus, parasites and/or fungus ineffective to infect or affect normally healthy cells while maintaining the biological usefulness of the blood or other fluids. For this purpose low voltage alternating current electric potentials are applied to the treatment vessel which are of the order of from about 0.2 to 12 volts and produce current flow densities in the blood or other fluids of from one microampere per square millimeter of electrode area exposed to the fluid being treated to about two milliamperes per square millimeter.

31 Claims, 6 Drawing Sheets

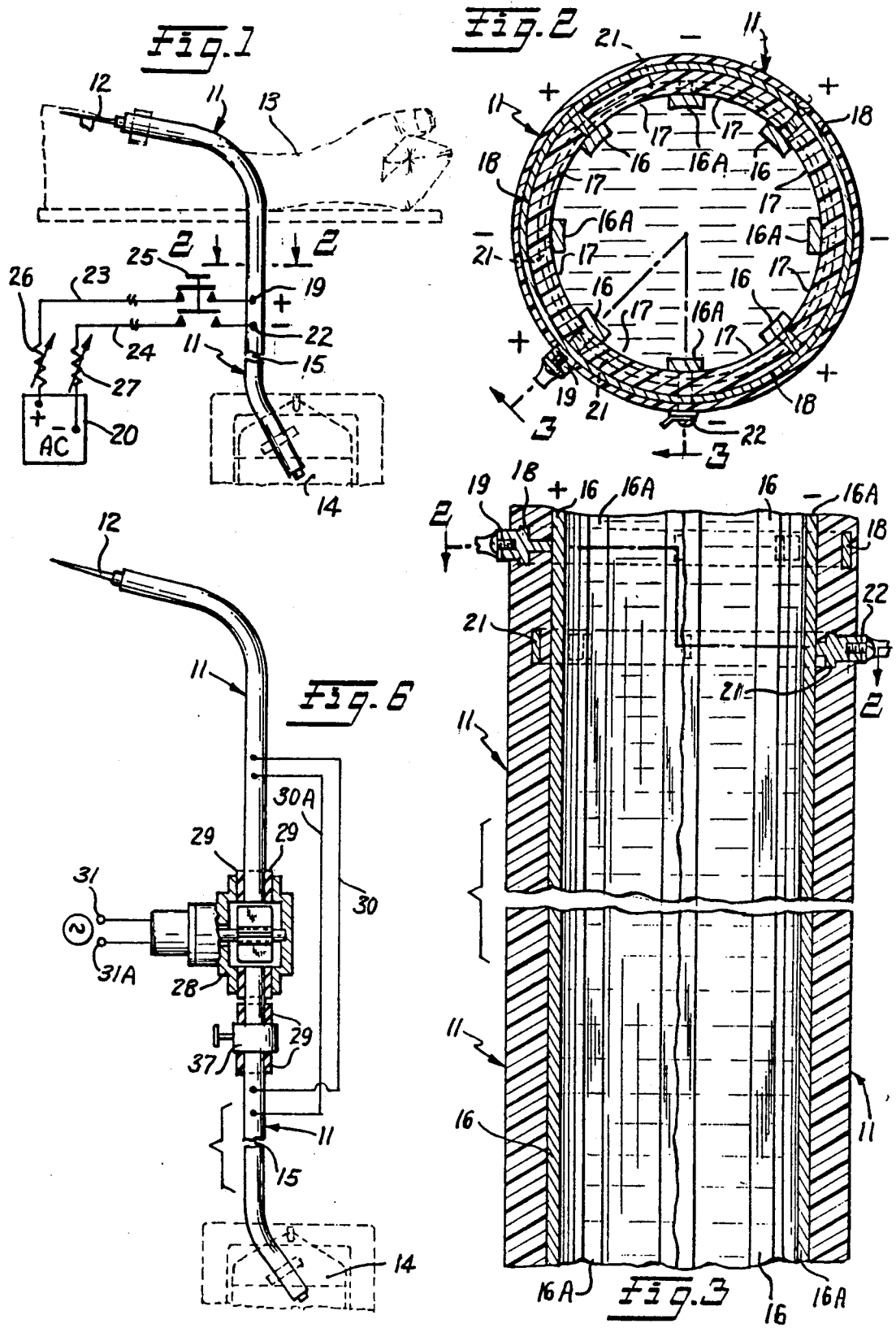

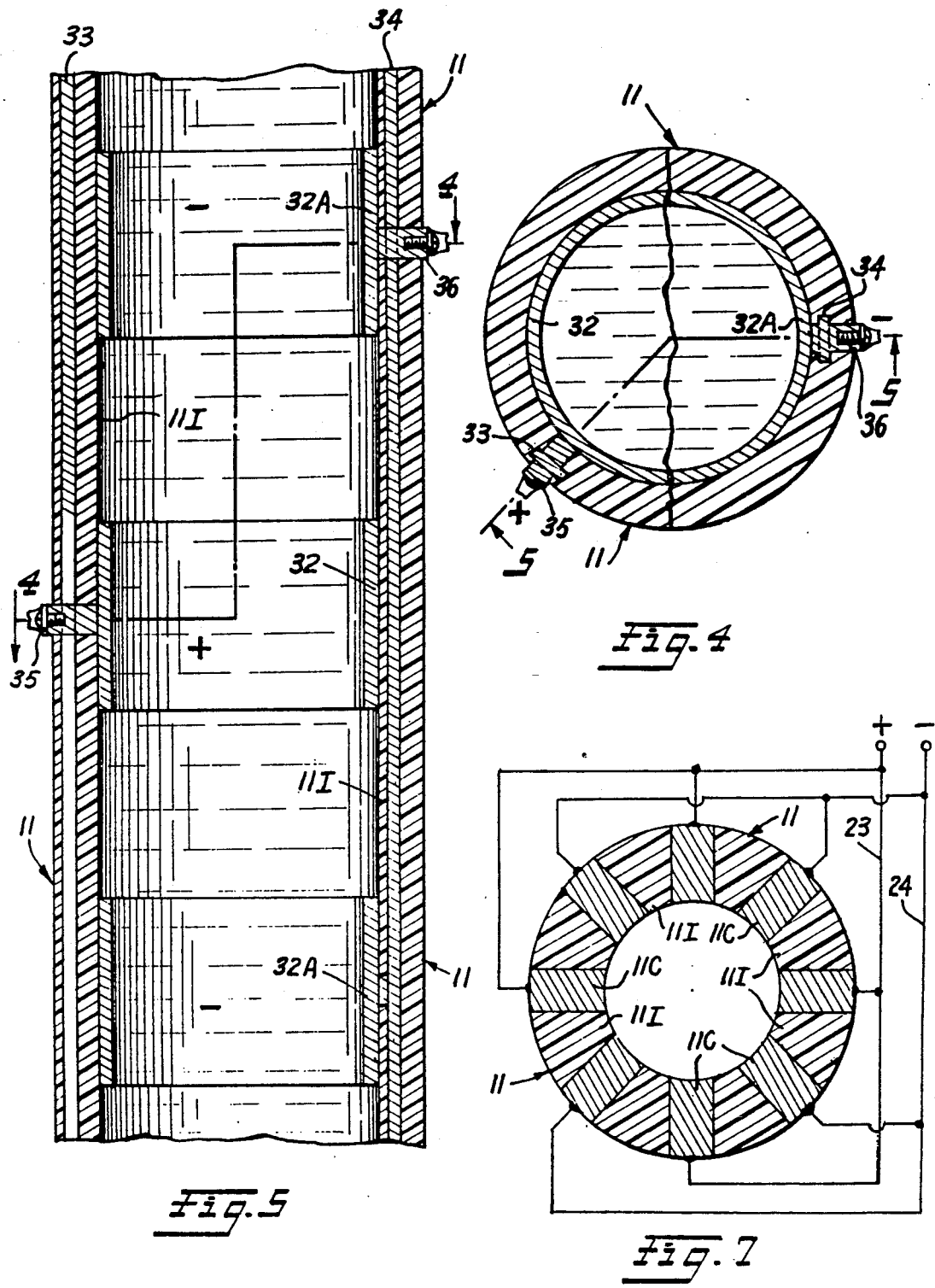

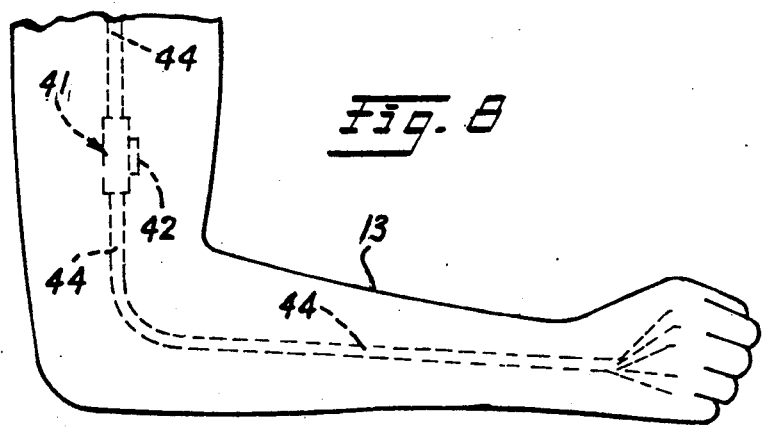
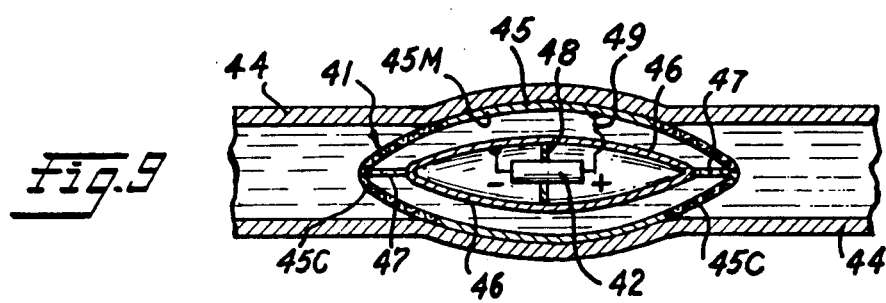
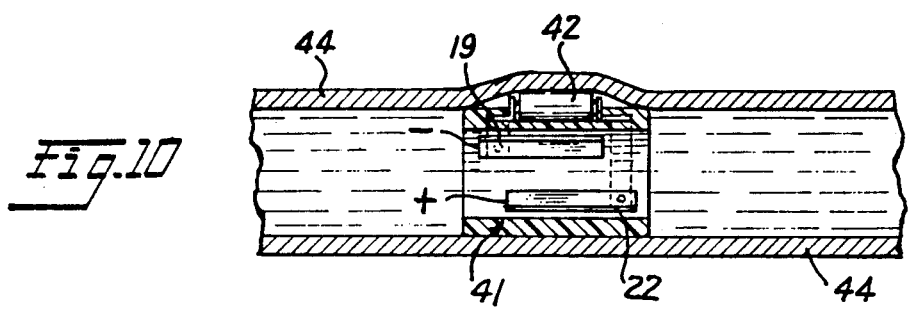
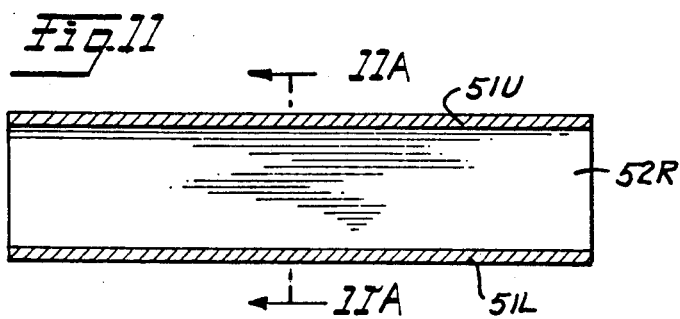
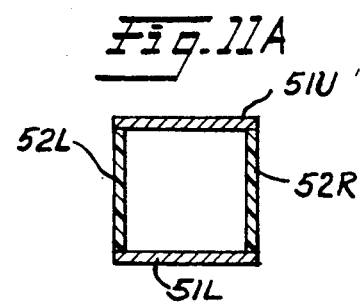

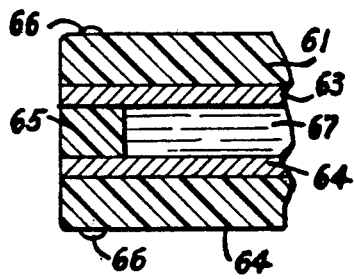
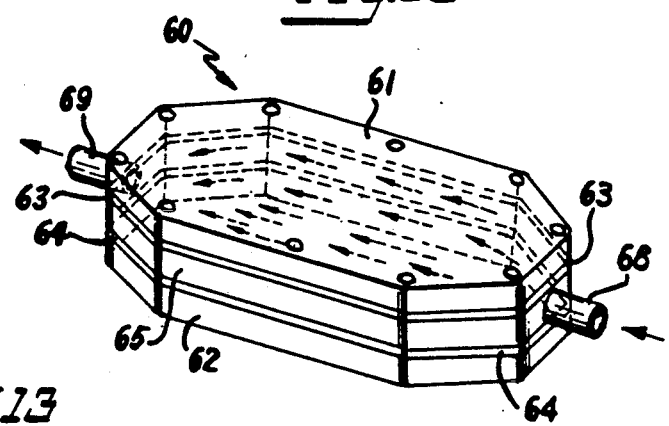
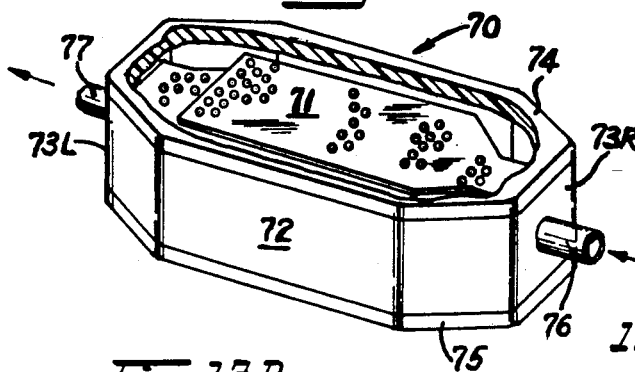
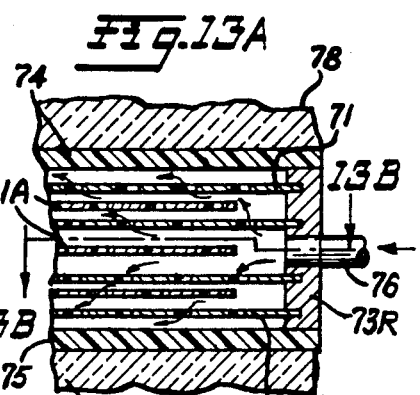
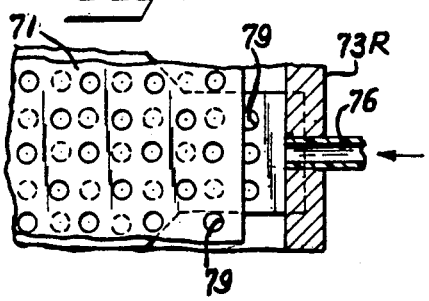
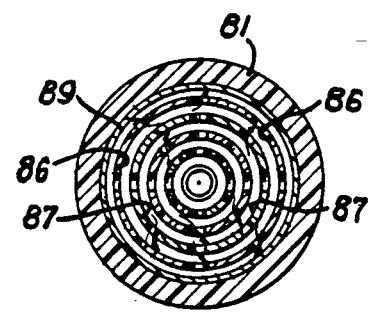
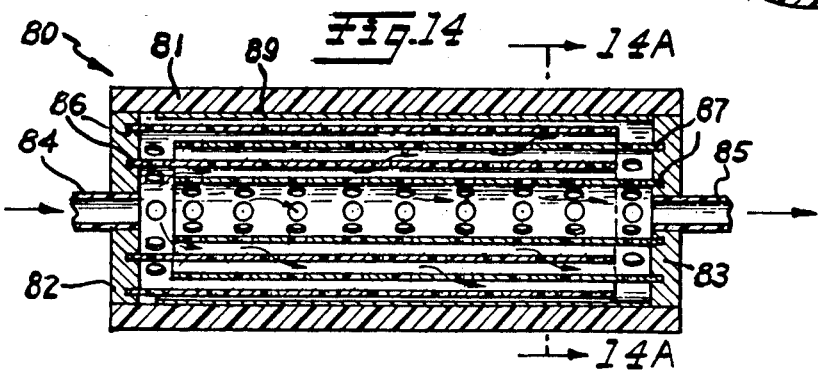

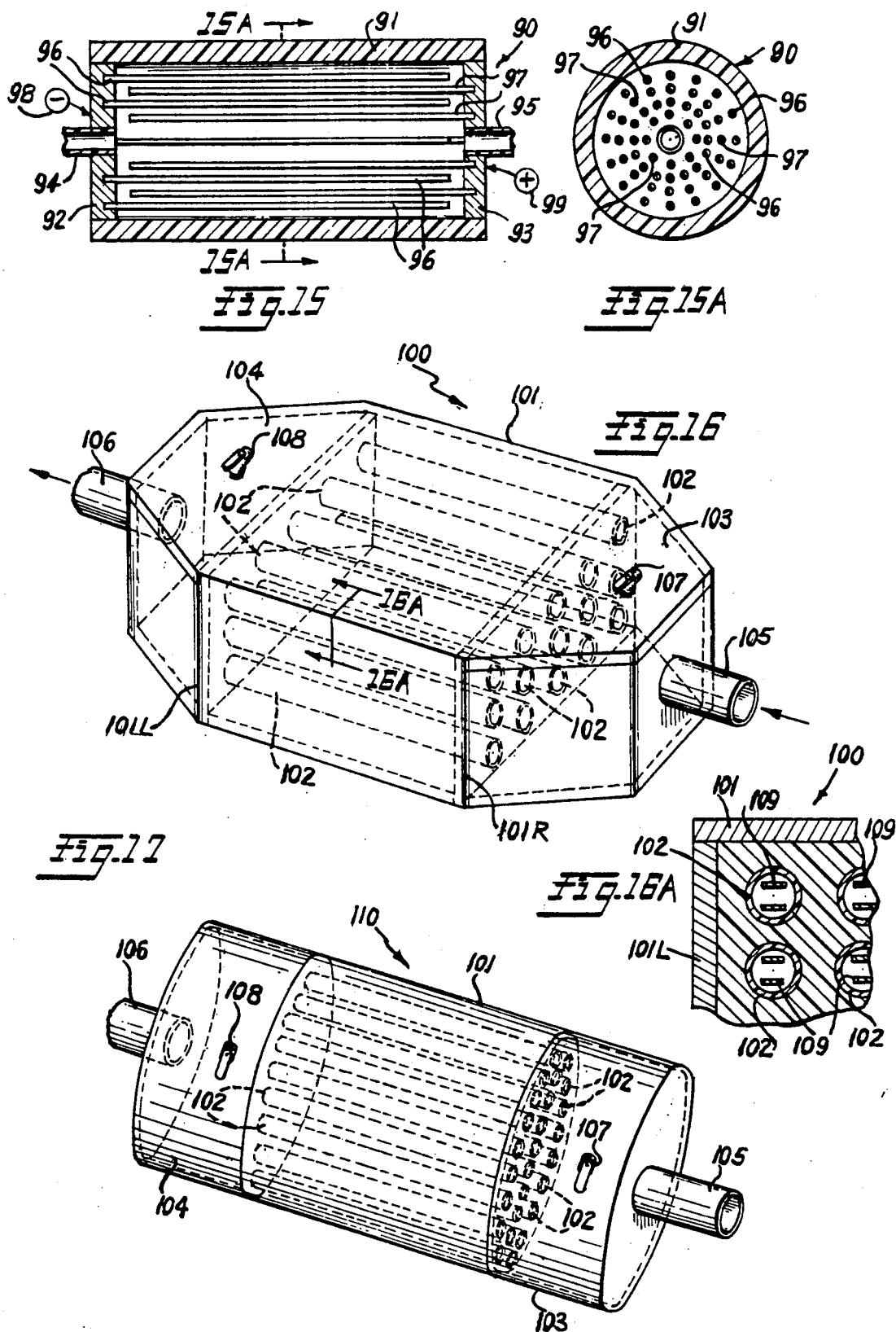

ALTERNATING CURRENT SUPPLIED ELECTRICALLY CONDUCTIVE METHOD AND SYSTEM FOR TREATMENT OF BLOOD AND/OR OTHER BODY FLUIDS AND/OR SYNTHETIC FLUIDS WITH ELECTRIC FORCES

FIELD OF INVENTION

This is a continuation-in-part application of prior U.S. patent application Ser. No. 07/562,721 filed Aug. 6, 1990, now abandoned This invention relates to novel electrically conductive methods and systems employing electrically conductive vessels provided with electrically conductive surfaces for use in subjecting blood and/or other body fluids and/or synthetic fluids such as tissue culture medium to direct treatment by alternating current electric forces.

BACKGROUND PROBLEM

It is now well known in the medical profession and the general public that blood collected in a blood bank from a large number of donors may be contaminated by contaminants such as bacteria, virus, parasites and/or fungus obtained from even a single donor. While screening of donors has done much to alleviate this problem, the screening of donors can and does miss occasional donors whose blood is unfit for use. When this occurs and the unfit blood is mixed with otherwise usable blood, the entire batch must be discarded for transfusion purposes. Because of this problem, the present invention has been devised to attenuate any bacteria, virus (including the AIDS HIV virus) parasites and/or fungus contained in blood contributed by a donor to the point that any such contaminant is rendered ineffective for infecting a normally healthy human cell, but does not make the blood biologically unfit for use in humans. Similar problems exist with respect to treatment of other body fluids, such as amniotic fluids. The treatment method and system is also applicable to mammals other than humans.

In addition to the above, there is a need for methods and systems for the treatment of blood and other body fluids both in in-situ processing wherein the treated blood and/or other body fluids are withdrawn from the body, treated and then returned to the body in a closed loop, recirculating treatment process that is located near but outside the patient's body, or the treatment can be effected through implanted treatment system components.

In co-pending United States application serial No. 07/615,800 entitled "Electrically Conductive Methods and Systems for Treatment of Blood and Other Body Fluids with Electric Forces"-Steven Kaali and Peter M. Schwolsky, inventors, filed concurrently and co-pending with this application, a similar treatment method and system employing direct current excitation potentials is described and claimed. The disclosure of co-pending application Ser. No. 07/615,800 hereby is incorporated into this application in its entirety.

SUMMARY OF INVENTION

The present invention provides new electrically conductive methods and systems using alternating electric current excitation potentials for treating blood and/or other body fluids, such as amniotic fluids, and/or synthetic fluids such as tissue culture medium from a donor to a transfusion recipient or to a storage receptacle, or for recirculating a single donor's or patient's blood or other body fluids. The treatment can be accomplished in a treatment system external of the body or by implant devices for purging contaminants using a novel electrically conductive vessel for direct electric treatment of blood or other body fluids, such as amniotic fluids, with alternating current electric field forces of appropriate electric field strength to attenuate such contaminants to the extent that bacteria, virus, fungus, and/or parasites contained in the blood or other body fluids are rendered ineffective to infect and/or affect normally healthy human cells. The treatment, however, does not render the blood or other body fluids biologically unfit for use in humans or other mammals after the treatment. The new methods and systems according to the invention achieve these ends without requiring time consuming and expensive processing procedures and equipment in addition to those normally required in the handling of blood or other body fluids or synthetic fluids. The invention can be used to achieve the electric field force treatment during the normally occurring transfer processing from a donor to a recipient or to a collection receptacle, or recirculation of a single donor's or patient's blood or other body fluids, such as amniotic fluids.

BRIEF DESCRIPTION OF DRAWINGS

The above and many other objects, features and attendant advantages of this invention will be appreciated more readily as the invention becomes better understood from a reading of the following detailed description, when considered in connection with the accompanying drawings, wherein like parts in each of the several figures are identified by the same reference characters, and wherein:

FIG. 1 is a diagrammatic, fragmentary, elevational view of a new blood transfer system using a novel alternating current electrically conductive treatment vessel in the form of conductive tubing to directly treat blood being transferred to a storage receptacle with electric field forces according to the invention;

FIG. 2 is an enlarged, horizontal cross sectional view of the novel electrically conductive tubing treatment vessel taken across lines 2—2 of FIG. 1;

FIG. 3 is a longitudinal, vertical sectional view of the novel electrically conductive tubing treatment vessel taken along the staggered section lines 3—3 of FIG. 2;

FIG. 4 is a view similar to FIG. 2 showing a different construction of the novel electrically conductive tubing treatment vessel;

FIG. 5 is a view similar to FIG. 3, taken along the staggered section lines 5—5 of FIG. 4;

FIG. 6 is a diagrammatic, fragmentary, elevational view showing a different modification of a novel blood transfer system using a novel electrically conductive tubing treatment vessel, and which employs a blood pump and a blood flow regulator;

FIG. 7 is an enlarged cross sectional view, similar to FIG. 2 that shows an electrically conductive tubing treatment vessel fabricated from longitudinally extending, integrally molded strips of alternate polarity, conductive polymer interconnected by integrally molded, insulating, longitudinally extending strips made of polymer or other insulating material;

FIG. 8 is a diagrammatic, fragmentary elevational view showing a different form of a blood transfer system according to the invention wherein a small electrically conductive vessel in the form of a short piece of tubing and a miniaturized battery power source are implanted in the arm of a human being to provide a novel electrically conductive blood and other body fluid treatment system which operates in a closed loop, recirculating manner;

FIG. 9 is a partial, diagrammatic sectional view of the upper arm portion of a human being and shows in greater detail the construction of a specially designed miniaturized, electrically conductive treatment vessel with associated miniaturized battery electric power source and DC to AC power converter for use in the implant treatment system shown in FIG. 8;

FIG. 10 illustrates the details of construction of a somewhat different form of miniaturized electrified treatment tubing for use in an implanted treatment system of the type shown in FIG. 8 and built according to the invention;

FIGS. 11 and 11A illustrate still a different construction for the electrified treatment tubing for use in practicing the invention wherein the tubing has a square or rectangular cross section with upper and lower conductive sides and intervening right and left sides separating the two conductive sides made from plastic or other suitable electrical insulating material;

FIG. 12 is a perspective top and side view of a novel electrified, closed, octagonally-shaped, flat, box-like treatment vessel having an enlarged cross sectional area relative to the cross sectional diameter of the inlet and outlet tubes supplying the interior of the treatment vessel;

FIG. 12A is a partial, cross sectional view of the enlarged treatment vessel shown in FIG. 12;

FIG. 13 is a perspective view of a second form of enlarged cross sectional area treatment vessel having an exterior shape similar to that of FIG. 12, but wherein the electrically conductive electrodes of the treatment vessel comprise interleaved conductive plates with one set of alternate ones of the plates being electrically insulated from the remaining set, and wherein different polarity electric potentials are applied to the respective sets. If desired, the electrode plates may be formed from an electrically conductive porous material;

FIG. 13A is a partial, cross sectional view taken through the electrically conductive treatment vessel shown in FIG. 13;

FIG. 13B is a sectional view taken through staggered line 13B—13B of FIG. 13A;

FIG. 14 is a longitudinal sectional view of still a different form of enlarged diameter electrified treatment vessel wherein the vessel is in the form of an elongated cylinder, and the sets of conductive electrodes mounted therein are concentrically arrayed within the interior of the treatment vessel and maintained at different electric potentials;

FIG. 14A is a cross sectional view of FIG. 14 taken through plane A—A;

FIG. 15 is an enlarged longitudinal sectional view of still another form of an enlarged cross sectional area treatment vessel according to the invention wherein the electrically conductive electrodes of the treatment vessel are comprised by longitudinally extending needle-like electrodes with alternate ones of the needle-like electrodes being provided with opposite polarity electric potentials;

FIG. 15A is a cross sectional view of the treatment vessel shown in FIG. 15 taken through plane A—A of FIG. 15;

FIG. 16A is a partial cross-sectional view taken through 16A—16A of FIG. 16;

FIG. 16 is a perspective view of still another form of enlarged cross sectional area treatment vessel according to the invention wherein the treatment vessel comprises a relatively large block of insulating material having parallel, longitudinally extending, open ended tubes formed through its length. The tubes are provided with electrically separated, opposed, parallel extending conductive plate electrodes which have opposite polarity electric potentials applied thereto. The ends of the tubes open into and are supplied from, or supply, respective reservoirs formed on the respective ends of the central block of insulating material containing the tubes, with inlet and outlet conduits for body fluids to be treated connected to the free ends of the respective reservoirs;

FIG. 17 is a perspective view of an enlarged cross sectional area treatment vessel similar to FIG. 16 wherein the body of the treatment vessel is cylindrical in nature;

BEST MODE OF PRACTICING INVENTION

Figure 18:
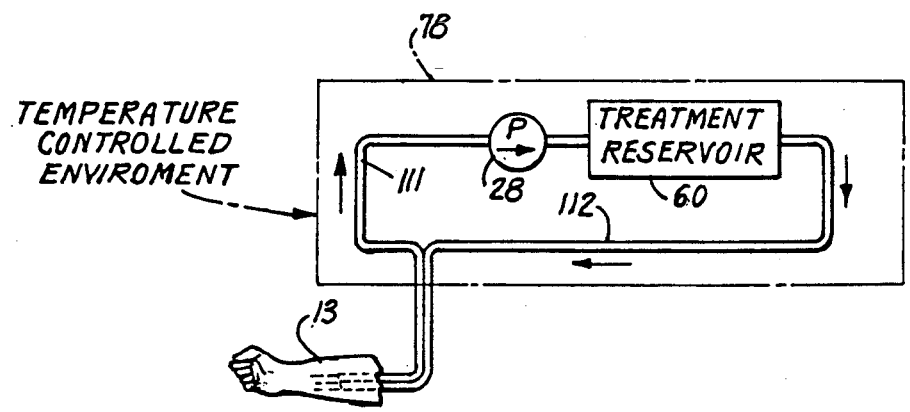
FIG. 18 is a diagrammatic, fragmentary elevational view of a human blood or other body fluid treatment system according to the invention employing one of the larger cross sectional dimension fluid treatment vessels shown in any one of FIGS. 12-16 of the drawings, and which is suitable for use in a continuous flow through recirculating body fluid treatment system.

FIG. 1 is a schematic illustration of one form of a novel blood and other body fluid treatment system according to the invention. FIG. 1 shows an electrically conductive blood and/or other body fluid treatment vessel constructed according to the invention which is in the form of intravenous tubing 11 interconnected between a hypodermic needle 12 and a blood storage receptacle 14. The needle 12 is inserted in an artery or vein of the arm 13 of a blood donor and the tubing 11 leads from the arm 13 to the receptacle 14. Alternatively, the system could be set up to transfer blood from the storage receptacle 14 to the arm of a recipient or could be designed to recirculate the blood through electrified tubing 11 back to the donor. The electrically conductive tubing 11 may be of any desired length as indicated by the break at 15 so that it can be appropriately set up to lead from a comfortable position for the donor from whose arm 13 the blood is being taken to a proper storage location for the receptacle 14. The greater the length of the electrified portion of tubing 11, then the more extended is the exposure of the blood (or other body fluid) to the electric field force effects and low level, biologically compatible current flow through the body fluid being treated thereby assuring adequate electrification treatment of the fluid without impairing the biological usefulness of the blood or other body fluid being treated.

FIG. 2 is a cross sectional view of the electrically conductive tubing 11 taken through plane 2—2 of FIG. 1. The tubing 11 may be from 1 to about 20 millimeters in inside diameter, although it may be larger or smaller in diameter depending upon the intended application. For example, if the blood transfer system is for the purpose shown in FIG. 6, then the tubing may have a cross sectional dimension of about 5 millimeters. However, if the intended use is in an implanted blood treatment system, such as shown in FIG. 8, then the tubing diameter must be designed to result in a flow-through rate corresponding to the natural circulatory blood flow rate of the patient in which the system is implanted, and must be long enough to assure effective electrification treatment at the flow rate selected. The tubing 11 is formed from plastic, rubber, medical grade polymer, or other suitable material which is compatible with human fluids and/or tissue. A plurality of physically separated, electrically conductive surface segments form opposed, parallel electrodes shown at 16 and 16A on the inside of tubing 11 from electrically conductive materials such as platinum, platinum alloys, silver, silver or platinum covered alloys, or other similar conductive materials such as conductive polymers, or silver or platinum covered polymers which are compatible with human fluids and tissue. The spacing between opposed electrodes 16 and 16A is of the order of 1 to 19 millimeters and perhaps may be more or less dependent upon the application and the conductivity of the body fluids being treated.

FIG. 3 is a longitudinally extending sectional view along the axis of tubing 11 taken through staggered section lines 3—3 of FIG. 2. From FIG. 3 of the drawings it will be seen that the electrically conductive surface segments 16 and 16A all comprise longitudinally extending, zebra-like stripe or strip electrodes which extend longitudinally in parallel with the longitudinal axis of the tubing 11. In between each longitudinally extending conductive stripe electrode 16 or 16A is a longitudinally extending electric insulating area 17 which electrically isolates the alternate electrically conductive, zebra-like stripe electrodes 16 and 16A one from the other.

As best shown in FIG. 3, a first set of alternate electrically conductive surface stripes 16 are electrically connected in common to a first annular terminal buss 18 which circumferentially surrounds the tubing 11 and is embedded within the sidewalls of the tubing 11 at a suitable point along its length. The design is such that the first annular terminal buss 18 is electrically isolated from the remaining second set of alternate, electrically conductive surface stripe electrodes 16A and is electrically connected through a conductor terminal 19 to an alternating current source of electric excitation potential. AC source 20 may comprise the output from an AC to AC voltage converter for converting 110 volt AC potential to the desired 0.2 volts to 12 volts for use in the invention. For those treatment systems which are to be implanted as described hereafter, the AC source may comprise a miniaturized DC to AC converter for converting the DC voltage from a miniaturized battery to low voltage (0.2 to 12 volts) AC. As best depicted in FIG. 2, all of the first set of positive electrically conductive stripes 16 are physically and electrically connected in common to the first annular terminal buss 18 so that all of the conductive stripes 16 are maintained at a constant, alternating current electric excitation potential.

A second annular terminal buss 21, which circumferentially surrounds the tubing 11, is embedded within the tubing 11 at a point along its length displaced from the position of the first annular terminal buss 18 and is spaced inwardly towards the inside diameter of the tubing relative to the first annular buss 18. By this arrangement it is possible to electrically connect the remaining second set of alternate electrically conductive surface stripes 16A in common to the second annular terminal buss 21 in a manner such that the second annular terminal buss is electrically isolated from the first annular terminal buss 18 as well as the first set of alternate electrically conductive surface stripes 16. As shown in FIG. 3, the second annular terminal buss 21 is provided with an outside terminal conductor connection 22 for connecting the annular buss 21 and annular buss 18 across AC source 20 as shown in the system drawing of FIG. 1. The second set of alternate electrically conductive surface stripes 16A are all provided with internal connector studs which physically and electrically connect all of the 16A stripes in common to the second annular terminal buss 21 so that all of these conductive stripes will be maintained at a potential opposite to that from the potential applied to the first set of electrically conductive stripes 16 by annular buss 18.

As described earlier, the AC source of electric potential 20 may constitute an AC to AC converter for converting 110 volt AC to 0.2 to 12 volt AC or a DC to AC converter for converting 12 volt DC to 0.2 to 12 volt AC. The AC source 20 is connected to the conductor terminals 19 and 22 through electric supply conductors 23 and 24 preferably by a double pole, double throw, on-off control switch 25. In preferred embodiments of the invention, voltage controlling variable resistors 26 and 27 also are included in the electric supply conductors 23 and 24 in order to control the value of the excitation voltage developed between the alternate sets of conductive surface stripes 16, 16A.

In operation, the donor whose blood is to be taken, or the recipient who is to be given blood, or is to have his or her blood recycled, is made comfortable on a cot with his or her arm 13 extended and the interconnecting electrically conductive tubing 11 having the hypodermic needle 12 for withdrawal, or supplying, or recycling of blood set up as shown in FIG. 1. When both the donor/recipient and the system is in readiness, the control switch 25 is closed so that an electric field is built up across the oppositely disposed electrically conductive zebra-like stripes 16, 16A, etc. Voltages of the order of from 0.2 to 12 volts are applied to the conductive surfaces 16, 16A For this purpose it is important to note that the hypodermic needle should be electrically isolated via conventional electrically insulating IV tubing from any of the zebra stripe electrodes 16, 16A so that the donor/recipient does not receive a shock. By this precaution, he or she will not even be aware of the existence of the electric field within the electrically conductive tubing 11. With the treatment system thus conditioned, the hypodermic needle is inserted into a vein in the donor's/recipient's arm and blood is withdrawn, given, or recycled through the tubing 11.

As the blood passes through the electric fields produced within the electric conductive tubing 11 it will be subjected to and treated by biologically compatible electric current flow through the blood or other body fluid with a current density of from one microampere per square millimeter (1 $\mu A/mm^2$) of electrode cross sectional area exposed to the fluid to about two milliamperes per square millimeter (2 mA/mm$^2$) dependent upon field strength of the electric field gradient existing between electrodes 16 and 16A, the space between the electrodes 16, 16A and the conductivity (resistivity) of the body fluid being treated. Recent experiments have proven that exposure to electric fields induced by supply voltages in the range produces electric current flow through blood of the order of 1 to 100 microamperes. Effectiveness is dependent upon length of time of treatment in conjunction with the magnitude of the biologically compatible current flow. For example, treatment of virus in media at 100 microamperes for 3 minutes has been observed to substantially attenuate (render ineffective) the AIDS virus. Similar treatment at other field strength values and lengths of time will have a similar attenuating effect on bacteria, virus, parasites and/or fungus which are present in blood or other body fluids being treated. By controlling the length of time and field strength values that blood is subjected to the electric field forces, undesirable contaminants such as virus, bacteria, fungus and/or parasites will be adequately attenuated to the point that they are rendered ineffective by the sustained action of the electric current flow as the blood travels from the hypodermic needle 12 to the storage bag 14, or vice versa, or in a recycling mode. The length of travel of the blood through the sustained electric field induced current flow also can be adjusted so that the blood is subjected to the electric field force for time periods of the order of from one to six minutes at least. At the current values noted above this is believed adequate to attenuate (render ineffective) bacteria, virus (including the AIDS virus), parasites and/or fungus entrained in blood or other body fluids, but does not render the fluids unfit for human use or impair their biological usefulness.

The species of the invention shown in FIGS. 2 and 3 is advantageous since it is possible to fabricate the treatment tubing by preforming the conductive segments 16 and 16A on the tubing walls while it is in a flat planar condition, and then rolling the walls into tubular form using a suitable mandrel. The adjoining longitudinal edges of the planar member after rolling are thereafter heat sealed along a longitudinally extending seam located within one of the electrically insulating sections 17. Particular attention must be paid to the juncture of the ends of the annular terminal busses 18 and 21 during the rolling and heat sealing steps to assure that good electrical interconnection and continuity at these junctures of the annular terminal busses is provided in the completed treatment tubing. The conductive electrode segments 16, 16A may be electro-deposited, chemically formed, separately formed conductive polymer surfaces, or conductive foil or wires adhesively secured to the side walls of the tubing 11 in advance of the rolling and sealing using techniques well known in the printed circuit and integrated circuit manufacturing technologies.

FIG. 6 is a diagrammatic, fragmentary, elevational view of a modified blood treatment system using the novel electrically conductive treatment tubing in accordance with the invention. In the FIG. 6 embodiment of the invention, a blood pump 28 of conventional, commercially available construction is inserted in the tubing 11 at some point along its length. The blood pump 28 is electrically isolated from the zebra striped conductive surfaces 16, 16A by suitable insulators 29 formed on the blood input-output connections of pump 28. Provision for electrically bypassing the blood pump 28 (if need be) is made through the shunt conductors 30, 30A which maintain electrical continuity of the alternating current excitation potential applied to the conductive stripes 16, 16A on each side of pump 28. For convenience, the alternating current excitation source 20 and its connection to the electrically conductive tubing 11 has not been shown in FIG. 6 but would have to be provided. A separate source of excitation current for running the blood pump 28 is provided from a conventional 110 volt alternating current source through the input terminals 31, 31A.

In systems employing a blood pump, it may be desirable in some applications to provide a blood flow regulating valve 37 inserted in the system at the output of blood pump 28 and within the by-pass loop 30, 30A for the conductive stripes 16, 16A. By thus controlling blood flow, the electrified transfer system safely can be employed in a closed loop recycling system for withdrawing blood from a patient, electrically treating the blood as described above and then returning the electrically treated blood to the patient. This procedure is referred to herein as recycling. The system of FIG. 6 also can be used in those situations where the blood flow of a donor's blood is not sufficient to assure supply of an adequate amount of blood to or from the collection receptacle 14 or other recipient. It may also be desirable to have a blood flow regulating valve such as 37 in non-pump systems.

FIGS. 4 and 5 of the drawings show another embodiment of the invention wherein the electrically conductive treatment tubing 11 includes electrically conductive electrode segments 32 and 32A which are in the form of zebra stripes that extend radially around the inside diameter of tubing 11 in spaced-apart, alternating polarity, conductive annular bands 32 and 32A separated by insulating surface bands 11I which serve to electrically isolate the respective first set of conductive zebra stripes 32 from the second set of conductive zebra stripes 32A. The first set of alternate ones of the electrically conductive annular stripes 32 are electrically connected in common to a first longitudinally extending terminal buss bar 33 that is embedded within tubing 11 in parallel with the longitudinal axis of the tubing and electrically isolated from the remaining second set of alternate electrically conductive annular stripes 32A. The first longitudinally extending terminal buss bar 33 is designed for connection to one output terminal of a source, such as 20, of alternating current electric excitation potential through a supply conductor connection 35 on the exterior surface of the tubing 11.

A second longitudinally extending terminal buss bar 34 is embedded within the body of tubing 11 and is electrically connected to the remaining second set of alternate electrically conductive annular stripes 32A. The second longitudinally extending terminal buss bar 34 is electrically isolated from the first longitudinally extending terminal buss 33 and the first set of alternate electrically annular stripes 32. Terminal buss bar 33 is designed for connection to a second output terminal for the alternating current source of electric excitation potential. For this purpose an input supply conductor connection 36 is directly connected through the exterior surface of tubing 11 and to the second longitudinally treatment extending terminal buss bar 34.

In operation, the embodiment of the invention shown in FIGS. 4 and 5 is physically arranged in a blood treatment system in the manner illustrated in FIG. 1 of the drawings with the positive polarity and negative polarity zebra annular stripes being connected to the respective output terminals of AC source 20 via control switch 25. If required, a blood pump such as 28 and blood flow regulating valve 37 shown in FIG. 6 can be included in the blood transfer system employing electrified tubing as shown in FIGS. 4 and 5.

Similar to the system shown in FIG. 1, a blood transfer system employing the embodiment of the invention shown in FIGS. 4 and 5 would be electrically excited in advance of injection of the hypodermic needle 12 into the arm of a blood donor so that all blood passing through the tubing 11 will be subjected to electric forces produced between the alternate polarity annularly formed conductive bands 32 and 32A. Experience with the invention will establish what length is required for the electrification field. However, for initial installations the length of the electrified field as related to the flow of blood through electrified tubing 11 should correspond to at least the 1–6 minute treatment time mentioned earlier. This is achieved by using an extended array of the alternate annular zebra bands 32 and 32A of adequate length to assure thorough subjection of blood to electric current flow produced between the alternating polarity zebra stripes 32 and 32A. The electric field force intensity applied to the blood by means of the electrified tubing is anticipated to be of the order of from 0.2 to 12 volts similar to the embodiment of the invention shown in FIGS. 1–3.

In place of supplying continuous alternating current excitation to the conductive stripes 16, 16A of FIGS. 2 and 3 or 32, 32A of FIGS. 4 and 5, it also is possible to excite these electrically conductive segments of tubing 11 with pulsed waveform direct current excitation potentials. For use in this manner, the pulse rate of the pulsed waveform excitation potentials must be sufficiently high to maintain continuous current flow through blood being treated. In addition, it may be desirable to couple a bank of storage capacitors in parallel across respective pairs of opposite polarity electrically conductive segments 16, 16A and 32, 32A where operation in a pulsed DC mode is desired.

FIG. 7 of the drawings is a cross sectional view of another embodiment of the invention which is substantially different from those previously described. In FIG. 7, the material used for fabrication of the tubing 11 is one of the new space-age polymer materials which can be either highly electrically conductive, insulating, or semiconducting and may have values of conductivity ranging from essentially fully conductive to insulating. In the embodiment of the invention of FIG. 7, the conductive surface areas on the inside diameter of the tubing 11 are actually formed into segments, such as 11C, of the cross sectional area of the tubing 11 fabricated from the highly conductive polymer material. The intervening segments of the tubing 11I which separate the conductive segments 11C are integrally formed from the highly insulating polymer material. Suitable positive polarity and negative polarity potentials are applied to the exterior surface areas of alternate ones of the sets of conductive polymer segments 11C from a source of electric potential via the conductors 23 and 24 as illustrated schematically in FIG. 7.

It will be appreciated that the embodiment of the invention shown in FIG. 7 is much simpler and hence less expensive to make in that it requires fewer processing steps than the embodiments of the invention shown in FIGS. 1–6. In other respects, the embodiment of the invention shown in FIG. 7 would be used in a blood transfer system similar to that shown in FIG. 1 or 6 with or without a blood pump 28 and blood flow regulating valve 37 to effect transfer of blood from a donor to a receptacle or recipient in the event of a transfusion or recycling. During the blood transfer process, again it would be necessary to provide alternating current excitation potentials across the spaced-apart, alternate sets of electrically conductive polymer segments 11C prior to passing blood through the tubing 11. This will assure that all of the blood being transferred is subjected to the electric field forces produced between the alternate conductive surfaces 11C. As a variation of the FIG. 7 embodiment, which visualizes that the segments 11C and 11I all extend longitudinally and parallel to the longitudinal axis of tubing 11, it would be possible, but more elaborate to design, to employ alternate radially surrounding annular conductive segments 11C and interlacing insulating segments 11I similar to FIG. 5, but such fabrication would require somewhat more complex terminal buss bar electric supply connections 23 and 24 than those shown in FIG. 7.

FIG. 8 is a fragmentary, diagrammatic, elevational view showing a form of blood treatment system according to the invention wherein a small electrically conductive vessel 41 in the form of a short piece of electrified tubing and a combined miniaturized DC to AC converter and battery power source 42 are implanted in the arm of a human being. The electrified tubing 41 may be in the form of any of the prior disclosed electrified tubing structures described with relation to FIGS. 1–7, but which are fabricated in miniaturized form so that the tubing 41 and power package 42 can be inserted in a section of or surrounding a vein 44 of the arm 13 of a patient whose blood is being treated. The implantation is such that the blood through the patient's vein 44 naturally is pumped through the short piece of electrified tubing 41 while circulating blood to the hand of the patient to thereby form a closed loop, recirculating, implanted treatment system that comprises an integral part of the circulatory system of the patient being treated. Because the parameters of such an implanted system are necessarily small, a single passage through the implanted electrified tube 14 may accomplish relatively little attenuation of contaminants in the blood. Therefore, it is the repeated passage of small portions of the patient's blood continuously twenty-four hours a day and for as many days as are needed which will gradually attenuate the contaminants to the point where they are rendered ineffective as described earlier.

FIG. 9 is a partial, fragmentary, sectional view of the upper arm portion 13 of a vein or artery of a patient in which a treatment system according to the invention has been implanted, and shows in greater detail the construction of a specialized, miniaturized, electrically conductive treatment vessel with associated miniaturized battery electric power source and DC to AC converter for use in an implanted treatment system as shown in FIG. 8. In FIG. 9, the electrified vessel 41 is in the form of an outer housing 45 that is in the shape of a football which is implanted within the interior walls 44 of an artery or a vein. The outer housing 45 is comprised by a central, cylindrically-shaped portion 45M of solid conductor such as platinum which is biocompatible with human blood and tissue and has integrally formed, conically-shaped porous ends 45C which are attached to and form an electrically conductive screen grid (at the same potential) as the mid portion 45M. The conical end portions 45C both are perforated and may be in the nature of a screen or mesh wire and of the same material composition as the mid portion 45M. Disposed within the outer housing 45 is a inner housing 46 which is tear-drop shaped and secured within the central portion 45M of the outer housing by suitable insulating support spider legs 47. The inner housing 46 likewise is formed from platinum or other suitable biocompatible conductive material and has supported within its interior a miniaturized AC source comprising a miniaturized battery and AC to DC converter 42 secured to the conductive walls of inner housing 46 by conductive support legs 48. The support legs 48 serve as terminal connectors from one terminal of AC power converter 42 to the inner housing 46 so that it is maintained at one polarity excitation potential. The remaining opposite polarity terminal of miniaturized AC source 42 is connected through an insulated conductor 49 to the central portion 45M of outer housing 45 whereby the entire outer housing including the meshed conical end portions 45C are maintained at an opposite polarity potential from the inner housing 46.

Prior to implantation in a patient, the electrified vessel shown in FIG. 9 is activated by connection to AC source 42 so that an electric field gradient is produced across the space between the inner and outer housings 45 and 46. Following implantation of the activated, electrified treatment vessel 41, its presence in a vein or artery will cause all blood flowing through the vein or artery to pass between the side walls of the inner and outer housings 45 and 46 so as to be subjected to the electric field force gradient existing in these spaces. The presence of the electric field forces will induce a current flow through the blood passing between the interior and outer housings as explained above which will result in attenuating bacteria, virus, parasites and/or fungus which are present in the blood as contaminants. Here again, because of the relatively small portion of the total blood flowing in a patient that will be treated by the device within a given time period, it is the repeated, recycling process treatment of the blood over a prolonged period of time that will result in attenuation of the contaminants in the blood to the point where such contaminants are rendered ineffective as described earlier.

In order to further assure adequate treatment of the blood of a patient receiving the implant device, it is recommended that the blood be treated in an external treatment processing facility such as described earlier in FIGS. 1 and 6 or to be described hereinafter with relation to FIGS. 18 and 19 in which the total capacity of the treatment system is greater whereby substantial attenuation effect can be achieved in a comparatively shorter time period yet to be determined, and then the in vitro implant treatment system such as shown in FIGS. 8, 9 and 10 can be used to maintain the attenuated condition and to prevent any subsequent build up of contaminants after the initial treatment, if determined to be desirable.

FIG. 10 is a fragmentary, diagrammatic view of a partial vein or artery 44 showing in greater detail the cylindrical or tubular electrified treatment vessel 41 originally described with relation to FIG. 8. This implant treatment vessel 41 is miniaturized so that it is in effect an open-ended cylinder in shape and has a diameter comparable to that of a large vein or artery and so that it can be grafted or implanted into the vein or artery as illustrated in FIG. 10. The tubular treatment vessel 41 may be designed pursuant to FIGS. 2 and 3 of the drawings, for example. For this application, the battery source of power and interconnected DC to AC converter 42 are annular in shape and are slipped over the tubular treatment vessel 41 in the manner shown. In FIG. 10 a longitudinal sectional view of the hollow annular-shaped treatment vessel 41 and AC power source 42 is illustrated. At the point where the battery driven AC power source 42 fits over the tubular treatment vessel 41, the respective terminals of the AC power source 42 are exposed to engage the corresponding positive and negative supply terminals 19 and 22 of the tube 41 so that the resulting structure has a minimum exterior profile to facilitate implantation. From a comparison of FIG. 10 to FIG. 9 of the drawings, it will be appreciated that the FIG. 9 treatment vessel introduces some flow restriction in the vein or artery in which it is implanted and for this reason the construction shown in FIG. 10 is preferred.

FIGS. 11 and 11A of the drawings illustrate a construction for the electrified treatment vessel 51 wherein the treatment vessel is in the form of square or rectangular cross sectionally-shaped open-ended tubing. The treatment tubing 51 provided with a square or rectangular shape so that provision of opposed, parallel conductive electrode surfaces 51U and 51L is greatly simplified as best seen in FIG. 11A of the drawings, which is a cross sectional view taken through plane 11A—11A of FIG. 11. By fabricating the upper and lower surfaces of the tubing 11 from electrically conductive material such as platinum, etc., and separating the upper and lower surfaces 51U and 51L by electrically insulating side walls 52R and 52L, provision of the electrically isolated, opposed, parallel electrode surfaces is simplified and the resulting treatment vessel introduces minimum restriction to flow of blood. By connecting the upper surface 51U to one terminal of the AC power source 42 and connecting the lower surface 51L to the opposite terminal, AC electrification of the interior area of the tubing wherein the fluids to be treated flow is readily achieved with a greatly simplified electrode structure. Variations of this structural feature wherein the side insulating surfaces 52R and 52L are curved with their concave surfaces facing each other and the cross sectional area of the upper and lower conductive surfaces 51U and 51L tailored to provide a desired current density, tubular treatment vessels such as shown in FIGS. 11 and 11A could be readily provided for use in implantation devices such as that illustrated in FIG. 8.

FIG. 12 is a perspective view of a novel, electrified, closed, octagonally-shaped, flat, box-like treatment vessel 60 according to the invention which provides an enlarged cross-sectional area relative to the cross sectional diameter of the inlet and outlet tubing supplying the interior of the treatment vessel whereby increased through-put of a fluid being treated can be achieved in a given time period. The treatment vessel 60 shown in FIG. 12 is comprised essentially of upper and lower, octagonally-shaped, flat insulating plates 61 and 62, respectively, of an insulating material which is compatible with human blood and/or other body fluids. Disposed immediately below and above the upper and lower plates 61 and 62 are octagonally-shaped, conductive electrode members 63 and 64, respectively, which are separated and electrically isolated one from the other by a surrounding electric insulating gasket member 65. The entire structure is sandwiched together and held in assembled relation by threaded thru-pins 66 as best seen in FIG. 12A of the drawings. The insulating gasket 65 which may be of teflon defines an open space 67 between the two conductive electrode members 63 and 64 into which the blood or other body fluid to be treated is introduced via inlet and outlet conduits 68 and 69. Alternating current electric potentials are applied across the respective conductive plates 63 and 64 to produce an electric field force across the intermediate space 67 through which the fluids being treated flow between electrode plates 63 and 64. By thus structuring the treatment vessel, increased treatment surface area is provided to the blood or other body fluid flowing through the space 67 whereby in a given time period an increased quantity of fluids can be treated.

FIG. 13 is a perspective view of another form of enlarged cross sectional area treatment vessel 70 having an exterior shape similar to that of the treatment vessel shown in FIG. 12. The electrified treatment vessel shown in FIG. 13 differs from that in FIG. 12, however, in the construction of its electrically conductive electrodes which comprise a plurality of interleaved, conductive, flat, electrode plates 71 and 71A. The electrode plates 71 are secured in and project inwardly from a right hand (RH) conductive end plate 73R as shown in FIG. 13A. The alternate set of flat electrode plates 71A are secured to and project inwardly from a corresponding conductive end plate 73L on the left hand end of the treatment vessel 70. The conductive end plates 73R and 73L and coacting insulating side plates 72 which insulate the conducting end plates from one another, form an octagonally-shaped box frame which is closed by upper and lower insulating top and bottom insulating plates 74 and 75. The conductive end plates 73R and 73L have a central opening formed therein into which inlet and outlet tubes 76 and 77 are secured as best seen in FIG. 13 for providing inlet and outlet flow through connection to the treatment vessel 70.

The alternate sets of flat electrode plates 71 and 71A extend parallel to one another and are provided with alternating current electric potentials supplied across the respective sets of interleaved electrode plates via the respective conductive end members 73R and 73L. If desired, the respective flat conductive electrode plates 71 and 71A may be fabricated from a perforated material as shown in FIG. 13B of the drawings. Also, it may be desirable that some form of thermal insulation, or a thermally controlled chamber be provided around the exterior of the treatment vessel 70 as indicated by the thermal insulation 78 shown in FIG. 13A.

In operation, electrified treatment vessel 70 shown in FIGS. 13, 13A and 13B functions in essentially the same manner as was described earlier with respect to FIGS. 1-7 to effect attenuation of contaminants such as bacteria, virus and fungus contained in blood and/or other body fluids being treated in the flow through treatment vessel of FIG. 13.

FIG. 14 is a longitudinal sectional view of still another form of enlarged cross sectional area, electrified treatment vessel 80. The treatment vessel 80 shown in FIG. 14 is in the form of an open-ended, elongated cylinder 81 whose cylindrical walls are fabricated from an insulating material which is biocompatible with human blood and/or other body fluids and whose open ends are closed by circular-shaped conductive end pieces 82 and 83. Inlet and outlet tubular openings 84 and 85 are provided to the interior of cylindrical housing 81 through centrally formed apertures in the circular end plates 82 and 83. Within the interior of the cylindrical, insulating housing 81 at least two, separate, concentric, perforated, cylindrically-shaped electrode members 86 and 87 are provided which extend longitudinally through the interior of the outer cylindrical housing 81. The first set of concentric, perforated, electrically conductive electrodes 86 is embedded in and supported by the conductive end plate 82 which serves as an electrical terminal for applying electric potentials to all of the concentric electrode member 86. Similarly, the concentric, perforated, conductive electrode member 87 is physically supported by and electrically connected to the conductive end plate 83 for the supply of alternating current potentials thereacross. Additionally, if desired, one or more additional perforated concentric electrode members similar to 86 may be spaced apart from the inner concentric electrode member 86 outwardly along the diameter of the circular end member 82 with additional perforated concentric electrode members 87 being sandwiched between the two electrode members 86 and spaced apart therefrom so as to provide an electric field force between all the spaced apart, separated electrically conductive electrode members 86 and 87. Additionally, if desired, a conductive surface 89 may be formed around the interior walls of the outer, insulating cylindrical housing member 81 and electrically connected to the conductive end plate 82 or 83. This will assure that the entire interior of the treatment 80 vessel cross sectional area is crossed by the electric field force and all blood or other body fluid passing the cylindrical housing member 81 is subjected to biologically compatible low electric current flow as a consequence of the alternating current electric fields produced between the different concentric electrode members including the coated surface 89 within the interior insulating housing member 81.

In operation, the embodiment of the invention shown in FIG. 14 and 14A operates in substantially the same manner as described with relation to earlier embodiments of the invention to assure production of biologically compatible electric current flow through the blood or other body fluid being treated in the treatment vessel 80.

FIG. 15 is a longitudinal sectional view of still another embodiment of an enlarged cross-sectional area treatment vessel 90. The treatment vessel 90 again comprises an outer, hollow, open-ended cylindrically-shaped, insulating body member 91 whose open ends are closed by electrically conductive, circular end plates 92 and 93, respectively. Inlet and outlet tubular openings 94 and 95 are provided through the central axial opening in the conductive end plates 92 and 93 for passage of blood and/or other body fluids being treated into the interior of the treatment vessel 90. The conductive end plates 92 and 93 have respective sets of opposite polarity potential needle-like electrodes 96 and 97, respectively, projecting therefrom inwardly into the interior of the treatment vessel 90. Alternating current electric potentials are applied to the respective conductive end plates 92 and 93 through respective AC supply terminals indicated at 98 and 99. If desired, and in order to assure complete saturation of the entire volumetric area within treatment vessel 90 with electric fields, a conductive coating similar to that shown at 89 in FIG. 14 can be provided to the inner surface of the hollow, cylindrically-shaped outer body member 91 of treatment vessel 90.

FIG. 15A is a cross sectional view taken through plane A-A of FIG. 15 and shows how the array of needle-like electrodes appear within the interior of the treatment vessel 90. In operation, the treatment vessel 90 will function in substantially the same manner as has been described previously with relation to earlier described embodiments of the invention.

FIG. 16 is a perspective view of still another form of enlarged cross sectional area treatment vessel 100 according to the invention and FIG. 16A is a partial cross sectional view taken through plane 16A—16A of FIG. 16. The treatment vessel 100 comprises a relatively large rectangular-shaped block 101 of electrical insulating material which is biocompatible with blood and/or other human body fluids. The insulating block 101 has a plurality of parallel, longitudinally extending, open-ended, tubular-shaped openings 102 formed therein through the entire length of the block. The tubes 102 are provided with electrically isolated, opposed, parallel extending conductive plate electrodes 109 as best shown in FIG. 16A, which have alternating current electric potentials applied thereacross. One set of these electrodes, formed for example by the lower electrode 109 in each tube, extend out to and engage a conductive surface coating formed on one end of the insulating block, for example 101R, and the remaining upper electrodes 109 form a second set which extend out of the left hand end of the tubes and contact a conductive coating formed on the remaining end 101L of block 101. Alternating current electric potentials are connected across the respective conductive surfaces 101R and 101L so that a potential difference exists between the sets of electrodes 109 within each longitudinally extending tube in block 101. The ends of the tubes 102 open into and are supplied from, or supply, respective header reservoirs 103 and 104 formed on the respective opposite ends of the block of insulating material 101. Each of the reservoirs 103 and 104 has a centrally formed opening for receiving either an inlet tube 105 applied to header 103 or an outlet tube 106 secured to header 104 for supply of blood or other body fluids to be treated to and from the treatment vessel 100. If desired, a blood pump or other fluid pump can be inserted between the supply tube 105 and header 103, or between outlet tube 106 and the or outlet from the header reservoir 104, or both. Alternatively, both inlet and outlet pumps can be used. In operation, the electrified treatment vessel 100 shown in FIG. 16 functions in the same manner as those species of treatment vessels described previously.

For some treatment applications, it may be desirable to provide exhaust vents such as shown at 107 and 108 in FIG. 16 to the inlet reservoir 103 and/or the outlet reservoir 104 with the vents that can be selectively operated by valves that can be automatically or manually controlled for venting off gases that might be trapped in the tops of reservoirs and which otherwise might interfere with the proper operation of the electrified treatment vessel. In a similar manner, suitable venting apparatus may be provided to other of the large cross sectional area electrified treatment vessels described previously.

FIG. 17 is a perspective view of still another enlarged cross-sectional area treatment vessel 110 which is similar in all respects to the treatment vessel shown in FIG. 16 with the exception that the body or block of insulating material 101 through which the elongate tubular openings are made, is cylindrically shaped as illustrated in FIG. 17. In other respects, the embodiment of the invention shown in FIG. 17 would be identical to FIG. 16 in the fabrication and operation of its component parts including the reservoir headers 103 and 104 and would operate in a similar manner.

FIG. 18 is a diagrammatic, sketch of a human blood or other body fluid treatment system employing one of the larger cross-sectional dimension fluid treatment vessels 60, such as any one of those shown in FIGS. 12-17 of the drawings. The particular fluid treatment system shown in FIG. 18 is for a continuous flow-through recirculating body fluid treatment wherein blood is withdrawn from the arm 13 of a patient and supplied through IV tubing 111 to a commercially available blood pump 28 and thence to an electrified treatment vessel 60. The treatment vessel 60 may be like any of the treatment vessels described with relation to FIGS. 12-17 of the drawings wherein the blood or other body fluid being treated is exposed to a low voltage, low current electric current flow for attenuating to the point of rendering them ineffective, any contaminants entrained in the blood, such as bacteria, virus and fungus. The treated blood appearing at the output of the treatment vessel 60 then is recirculated back through IV tubing 112 to the arm 13 of the patient whose blood or other body fluid is being treated. If desired, IV tubing 111 and 112 could also be treatment tubing such as described in FIGS. 1-7 and 11. This could provide double treatment for the fluid if that were desirable. In the event that the entire treatment does not take place in an air conditioned, temperature controlled room, then it may be desirable to provide a temperature controlled enclosure indicated by dotted lines 78 around at least the pump 28, electrified treatment vessel 60 and the interconnecting IV tubing sections 111 and 112 in order to assure maintaining a substantially constant viscosity of the blood or body fluid being treated.

Normally, the system of FIG. 18 would be used in a continuous flow-through recirculating treatment system wherein blood from the patient's arm 13 is supplied through pump 28 to the treatment vessel 60 where it is treated and then discharged back through tubing section 112 to the arm of the patient. The flow rate of the blood thus processed would be adjusted to correspond substantially to the natural flow rate of blood circulated through the patient's body to the extent possible.

In addition to operation in the above manner, it would also be possible to operate the system of FIG. 18 in a stopped-flow, batch treatment manner wherein the blood pump is intermittently stopped to allow for more extended electrical treatment of the blood or other body fluid contained in the treatment vessel 60 during the period of time (referred to as the dwell time) that the blood pump is stopped thereby assuring fuller electrification treatment and the greater attenuation of the bacteria, virus, parasites and/or fungus entrained in the blood.

Figure 19:
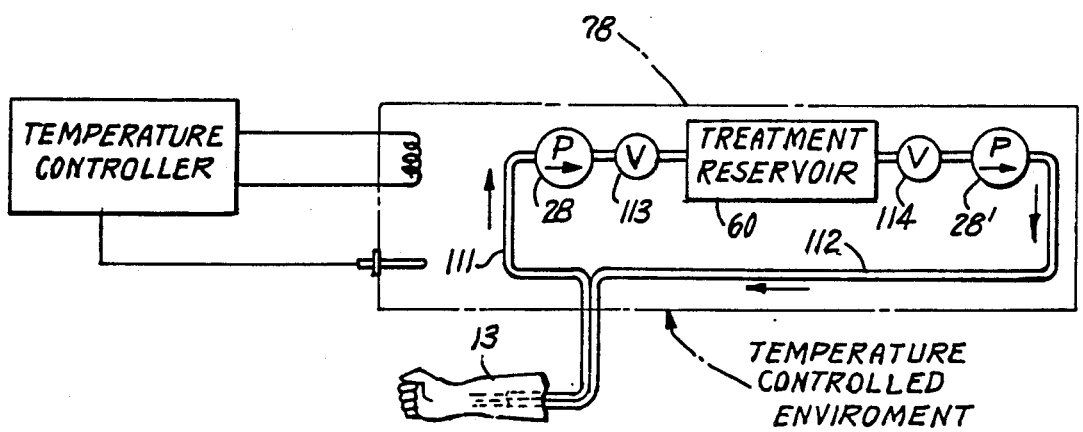
FIG. 19 is a diagrammatic, fragmentary elevational view of still another human blood or other body fluid, closed loop, recirculating treatment system according to the invention designed for use with the enlarged diameter fluid treatment vessels illustrated in FIGS. 12-16, and which employs both inlet and outlet fluid pumps on each side of the treatment vessel. With this arrangement the system can be operated in an intermittent manner to allow batch treatment of the body fluids to fully take place before passage of the body fluids being treated back to the patient.

FIG. 19 is a diagrammatic sketch of a form of closed loop, flow-through recirculating treatment system according to the invention that is somewhat similar to the system shown in FIG. 18. FIG. 19 differs from FIG. 18 in that an inlet pump 28 and an outlet pump 28' are connected to, respectively, the intake to and outlet from the electrified treatment vessel 60. If desired, an inlet control valve 113 and an outlet control valve 114 also can be interconnected between the inlet pump 28 and the intake to the treatment vessel 60 and between the output from the treatment vessel 60 and the intake to the outlet blood pump 28'. These inlet and outlet control valves indicated at 113 and 114 preferably are automatically operated in a time sequence which allows the system of FIG. 19 to be operated as a two pump, start-stop flow through system. When operated in this manner, the first pump 28 is allowed to operate and discharge blood from the arm 13 of the patient to be pumped into the treatment vessel 60 and thereafter is closed off with both the inlet and outlet valves 113 and 114 in their closed condition. At this point electrification treatment of the blood or other body fluid takes place for a predetermined, scheduled time period to assure adequate attenuation to the point of rendering ineffective the contaminant bacteria, virus, parasites or fungus. Upon completion of the pre-scheduled treatment period, the outlet valve 114 is opened and outlet pump 28' actuated to return the treated blood to the arm of the patient 13. Operation in this semi-continuous, start-stop, batch fashion will assure that adequate electrified treatment of the blood has been accomplished while achieving this end in a somewhat continuous manner suitable for use in a closed loop, recycling blood treatment process.

PRACTICAL USES OF INVENTION

While the disclosure herein presented has been directed to principally the electrical treatment of blood, it is believed obvious to those skilled in the art that the invention can be applied with corresponding effect to other body fluids which are electrically conductive for the treatment of contaminants such as bacteria, virus, parasites and/or fungus contained therein. Further, while voltages of the order of from about 0.2 volts to 12 volts AC have been indicated as preferable, it is possible that certain virus may be attenuated (or attenuated at a faster rate) if they are subjected to greater electric current magnitudes of the order of 500 microamperes for shorter time periods. Acceptable current magnitudes normally would require an excitation voltage of from 0.2 to 12 volts. However, in certain cases where faster or more complete attenuation of the contaminants in body fluids may be desired under certain circumstances and conditions, the excitation voltage supplied to the conductive tubing may in fact exceed the 0.2 to 12 volt range indicated for most treatments.

Although it is uncertain what is specifically causing the attenuation of the contaminants (virus, bacteria, parasites and/or fungus), some possible explanations have been put forward. One is that the attenuation is caused simply by the direct affect of the electric current and voltage. Another entails the following. When a voltage is applied to the electrodes, a small current will flow through the electrically conductive medium. The applied voltage and ensuing current will induce changes in the complex biologically active fluid. Current can flow through the media if positive and/or negative charges are transported through said media. The transport might induce changes in the charge distribution of the biologically active molecules thus changing their biological activity. Furthermore, the voltage and current can induce the production or elimination of different ions, radicals, gases and/or PH levels which may affect, alone or in combination, the biologically active molecules and/or cells. The above products of the electrical processes may either be very short lived and stay in the close proximity of the electrodes or can diffuse or mix in the bulk of the media and react with the biologically active molecules or cells to result in their attenuation.

Having described several embodiments of new and improved electrically conductive treatment methods and vessels for use in practicing the novel method for the treatment of blood and/or other body fluids with electric field forces and treatment systems employing the same, it is believed obvious that other modifications and variations of the invention will be suggested to those skilled in the art in the light of the above teachings. It is therefore to be understood that changes may be made in the particular embodiments of the invention described which are within the full intended scope of the invention as defined by the appended claims.

What is claimed is:

1. An electrically conductive vessel for direct electric treatment of bacteria, and/or virus, and/or parasites and/or fungus entrained in blood and/or other body fluids and/or synthetic fluids contained within or flowing through the vessel in the presence of electric field forces, said electrically conductive vessel being fabricated with only biologically compatible material contacting the fluid being treated and with an array of at least two or more spaced-apart, opposed electrically conductive electrode segments formed of biologically compatible conductive material on or in the interior surface of the vessel and exposed to blood or other fluids contained in or flowing through the vessel, said electrically conductive electrode segments being electrically isolated from each other and extending over or through a portion of the length of the vessel, and means for applying low voltage alternating current non-biologically damaging electric potentials to the electrically conductive electrode segments whereby electrical field forces are produced between the electrically conductive electrode segments that induce biologically compatible current flow through the blood and/or other fluids contained in or flowing through the vessel so as to attenuate bacteria, virus, parasites and/or fungus contained in the blood and/or other fluids by the action of the electric current flow therethrough to thereby render the bacteria, virus, parasites and/or fungus ineffective while not impairing and maintaining the biological usefulness of the fluids.

2. An electrically conductive vessel according to claim 1 wherein the low voltage alternating current electric potentials are in the range from about 0.2 volts to 12 volts and induce electric current flow densities in the blood or other fluids of from one microampere per square millimeter (1 $\mu A/mm^2$) to about two milliamperes per square millimeter (2 $mA/mm^2$).

3. An electrically conductive vessel according to claim 2 wherein the vessel is in the form of tubing and is inserted in a flow-thru blood treatment system between a hypodermic needle employed to withdraw and/or supply blood from a donor and/or to a recipient and/or a blood storage receptacle or to a patient in a blood recycling system.

4. An electrically conductive vessel according to claim 2 wherein the vessel is part of a system and is in the form of tubing and a blood pump is inserted in the tubing between a donor and a recipient or a receptacle, and the system further includes means for electrically isolating the blood pump from the electrically conductive vessel, means for regulating blood flow rate from the blood pump output and means for maintaining electrical continuity throughout a desired length of the conductive vessel.

5. An electrically conductive vessel according to claim 2 wherein the vessel is in the form of tubing and the electrically conductive electrode segments are in the form zebra stripes which extend longitudinally parallel with the longitudinal axis of the tubing with the alternate electrically conductive electrode stripes being separated by alternate electrically insulating stripes for electrically isolating the alternate electrically conductive electrode stripes one from the other, a first set of alternate ones of the electrically conductive electrode stripes being electrically connected in common to a first annular terminal buss formed on and circumferentially surrounding the tubing and electrically isolated from the remaining second set of alternate electrically conductive electrode stripes, said first annular terminal buss being designed for connection to one supply terminal of a source of alternating current electric excitation potential, and a second annular terminal buss circumferentially surrounding the tubing and electrically connected to the remaining second set of alternate electrically conductive electrode stripes, said second annular terminal buss being electrically isolated from the first annular terminal buss and the first set of alternate electrically conductive electrode stripes and being designed for connection to a second supply terminal of a source of alternating current electric excitation potential.

6. Electrically conductive tubing according to claim 5 wherein the tubing is inserted in a flow-thru blood treatment system between a hypodermic needle employed to withdraw and/or supply blood from a donor and/or to a recipient and/or a blood storage receptacle or to a patient in a blood recycling system.

7. Electrically conductive tubing according to claim 5 wherein a blood pump is inserted in the tubing between a donor and a recipient and/or a receptacle, and the tubing is a part of a system which further includes means for electrically isolating the blood pump from the electrically conductive tubing, means for regulating blood flow rate from the blood pump output, and means for electrically interconnecting the input and output sides of the tubing around the blood pump and the blood flow regulating means whereby electrical continuity is maintained throughout a desired length of the tubing.

8. An electrically conductive tubing according to claim 2 wherein the vessel is in the form of tubing and the electrically conductive electrode segments are in the form of zebra stripes which extend radially around the inside diameter of the tubing in alternating conductive and insulating annular bands whereby alternate conductive bands are electrically isolated one from the other by respective insulating bands, a first set of alternate ones of the electrically conductive annular electrode stripes being electrically connected in common to a first longitudinally extending terminal buss that is formed on the tubing in parallel with the longitudinal axis thereof and electrically isolated from the remaining second set of alternate electrically conductive annular electrode stripes, said first longitudinally ext ending terminal buss being designed for connection to a first supply terminal of a source of alternating current electric excitation potential, and a second longitudinally extending terminal buss electrically connected to the remaining second set of alternate electrically conductive annular electrode stripes, said second longitudinally extending terminal buss being electrically isolated from the first longitudinally extending terminal buss and the first set of alternate electrically conductive annular electrode stripes and being designed for connection to a second supply terminal of a source of alternating current electric excitation potential.

9. Electrically conductive tubing according to claim 8 wherein the tubing is inserted in a flow-thru blood treatment system between a hypodermic needle employed to withdraw and/or supply blood from a donor and/or to a recipient and/or a blood storage receptacle or to a patient in a blood recycling system.

10. Electrically conductive tubing according to claim 9 wherein a blood pump is inserted in the tubing between a donor and a recipient and/or a receptacle, and the tubing is part of a system that further includes means for electrically isolating the blood pump from the electrically conductive tubing, means for regulating blood flow from the output of the blood pump, and means for electrically interconnecting the input and output sides of the tubing around the blood pump and blood flow regulating means whereby electrical continuity is maintained through a desired length of the tubing.

11. An electrically conductive vessel according to claim 2 wherein the walls of the vessel itself are formed from electrically conductive polymer material that is compatible with human tissue and blood and/or other body fluids with the electrically conductive portions being formed into desired patterns of spaced apart electrically conductive electrode segments physically interconnected by integrally formed electrically insulating tubing walls portions which electrically isolate a first array of electrode segments from a second array of electrode segments.

12. An electrically conductive vessel according to claim 11 wherein the vessel is in the form of tubing and the electrically conductive electrode segments are in the form of zebra stripes which extend longitudinally parallel with the longitudinal axis of the tubing with the alternate electrically conductive electrode stripes being separated by alternate electrically insulating stripes for electrically isolating the alternate electrically conductive electrode stripes one from the other, a first set of alternate ones of the electrically conductive electrode stripes being electrically connected in common to a first annular terminal buss formed on and circumferentially surrounding the tubing and electrically isolated from the remaining second set of alternate electrically conductive electrode stripes, said first annular terminal buss being designed for connection to one supply terminal of a source of alternating current electric excitation potential, and a second annular terminal buss circumferentially surrounding the tubing and electrically connected to the remaining second set of alternate electrically conductive electrode stripes, said second annular terminal buss being electrically isolated from the first annular terminal buss and the first set of alternate electrically conductive electrode stripes and being designed for connection to a second supply terminal of a source of alternating current electric excitation potential.

13. Electrically conductive tubing according to claim 12 wherein the tubing is inserted in a flow-thru blood treatment system between a hypodermic needle' employed to withdraw and/or supply blood from a donor and/or to a recipient and/or a blood storage receptacle or to a patient in a blood recycling system.

14. Electrically conductive tubing according to claim 13 wherein a blood pump is inserted in the tubing between a donor and a recipient and/or a receptacle, and the tubing is part of a system which further includes means for electrically isolating the blood pump from the electrically conductive tubing, means for regulating blood flow from the output of the blood pump, and means for electrically interconnecting the input and output sides of the tubing around the blood pump and blood flow regulating means whereby electrical continuity is maintained throughout a desired length of the tubing.

15. An electrically conductive vessel according to claim 11 wherein the vessel is in the form of tubing and the electrically conductive electrode segments are in the form of zebra stripes which extend radially around the inside diameter of the tubing in alternating conductive and insulating annular bands whereby alternate conductive bands are electrically isolated one from the other by respective insulating bands, a first set of alternate ones of the electrically conductive annular electrode stripes being electrically connected in common to a first longitudinally extending terminal buss that is formed on the tubing in parallel with the longitudinal axis thereof and electrically isolated from the remaining second set of alternate electrically conductive annular electrode stripes, said first longitudinally extending terminal buss being designed for connection to a first supply terminal of a source of alternating current electric excitation potential, and a second longitudinally extending terminal buss electrically connected to the remaining second set of alternate electrically conductive annular electrode stripes, said second longitudinally extending terminal buss being electrically isolated from the first longitudinally extending terminal buss and the first set of alternate electrically conductive annular electrode stripes and being designed for connection to a second supply terminal of a source of alternating current electric excitation potential.

16. Electrically conductive tubing according to claim 15 wherein the tubing is inserted in a flow-thru blood treatment system between a hypodermic needle employed to withdraw and/or supply blood from a donor and/or to a recipient and/or a blood storage receptacle or a patient in a blood recycling system.

17. Electrically conductive tubing according to claim 16 wherein a blood pump is inserted in the tubing between a donor and a recipient and/or a receptacle, and the tubing is part of a system that further includes means for electrically isolating the blood pump from the electrically conductive tubing, means for regulating blood flow from the output of the blood pump, and means for electrically interconnecting the input and output sides of the tubing around the blood pump and the blood flow regulating means whereby electrical continuity is maintained throughout a desired length of the tubing.

18. A fluid treatment process for attenuating bacteria, and/or virus, and/or parasites, and/or fungus, existing in blood and/or other body fluids and/or synthetic fluids within a treatment vessel having only biologically compatible internal and conductive electrode surfaces therein contacting fluid being treated thereby maintaining the biological usefulness of the blood or other fluids being treated comprising subjecting the fluid within the treatment vessel to low voltage, low alternating current electric field forces within non-biologically damaging electric field forces for producing a biologically compatible current flow through the blood or other fluids for a predetermined period of time sufficient to attenuate bacteria and/or virus, and/or parasites and/or fungus contained in the blood or other fluids to thereby render them ineffective while maintaining the biological usefulness of the fluids being treated.

19. The product of the process according to claim 18.

20. A fluid treatment process according to claim 18 wherein the low voltage alternating current electric potentials are in the range from about 0.2 to 12 volts and induce electric current flow densities in the blood or other fluids of from one microampere per square millimeter (1 $\mu A/mm^2$) to about two milliamperes per square millimeter (2 $mA/mm^2$).

21. The product of the process according to claim 20.

22. A fluid treatment system for attenuating bacteria, and/or virus, and/or parasites, and/or fungus existing in blood and/or other body fluids and/or synthetic fluids being treated without biological damage to the blood or other fluids comprising an electrically conductive vessel formed at least in part of biologically compatible conductive material for contacting blood or other fluids to be treated, means for subjecting the blood or other fluids within the conductive vessel to low voltage, low alternating current electric field forces for producing biologically compatible current flow through the blood or other fluids for a predetermined period of time sufficient to attenuate bacteria and/or virus, and/or parasites, and/or fungus contained in the blood or other fluids to thereby render such contaminants ineffective while maintaining the biological usefulness of the blood or other fluids.

23. A fluid treatment system according to claim 22 wherein the low voltage alternating current electric potentials are in the range from about 0.2 to 12 volts and produce electric current flow densities in the blood or other body fluids of from one microampere per square millimeter (1 $\mu A/mm^2$) to about two milliamperes per square millimeter (2 $A/mm^2$).

24. A fluid treatment system according to claim 22 wherein the system comprises a plurality of components including an electric power source all of which the miniaturized and implanted in the body of a patient being treated to form a closed loop, continuous recirculating body fluid treatment system.

25. A fluid treatment system according to claim 22 wherein the conductive vessel is in the form of an open ended tube to allow flow-thru treatment of blood and other fluids and is miniaturized along with an electric power source for supply of alternating current electric potentials thereto whereby the system may be implanted in human beings and other mammals to operate as a continuous recirculating fluid treatment process.

26. A fluid treatment system according to claim 22 wherein the conductive vessel in the vicinity of the spaced-apart opposed electrically conductive electrode segments is provided with an enlarged cross sectional area wherein enlarged electrically conductive electrode segment surface areas are provided to act on the blood or other fluids flowing through the vessel thereby increasing the through-put and/or effectiveness of the treatment accomplished within the vessel for a given dwell time.

27. A body fluid treatment system according to claim 26 wherein the electrically conductive vessel comprises an enlarged rectangular-shaped body of electrical insulating material having a plurality of parallel, longitudinally extending tubular openings formed all the way through the insulating material from one end to the other and having spaced-apart electrically conductive metal strips secured to respective opposite sides of all of the tubes in opposed, parallel relationship, one set of corresponding conductive strips of all of the tubes extending out of the ends of each tube on one side or end of the body of electrical insulating material and contacting a conductive surface forming a terminal buss for all conductive strips of the set, and the remaining set of conductive strips projecting out of the opposite ends of the respective tubes on the opposite end of the insulating block to engage a conductive terminal surface, and header reservoirs formed on each of the ends of the body of electrical insulating material into which the ends of the tubular openings are connected, each header having a respective inlet or outlet opening for supply of blood and/or other fluids for treatment thereto.

28. A fluid treatment system according to claim 27 wherein the enlarged insulating clock member is cylindrically shaped and the header reservoirs at each end of the block member are correspondingly cylindrically shaped.

29. A fluid treatment system according to claim 27 wherein selectively operated gas vents are provided in the top of the respective header reservoirs of the electrically conductive vessel.

30. A fluid treatment system according to claim 26 wherein the electrically conductive vessel is in the form of an enlarged cross sectional area treatment vessel of substantially greater cross sectional area than the inlet and outlet conduits supplying body fluids to be treated to the vessel and wherein the enlarged cross sectional area vessel is included in a blood transfer system between a hypodermic needle employed to withdraw and/or supply blood from a donor and/or to a recipient and/or a blood storage receptacle or to a patient in a continuous flow-thru blood recycling system.

31. A fluid treatment system according to claim 30 wherein a blood pump is inserted in the flow path of the blood or other fluid either to or from the enlarged cross sectional area vessel, or both, and are located in a tubing system between the donor and recipient or receptacle, and the system further includes means for regulating blood flow rate from or to the enlarged cross sectional area treatment vessel via the inlet or outlet pumps or both.

* * * * *